United States Patent [19]

Wood et al.

[11] Patent Number: 4,857,067
[45] Date of Patent: Aug. 15, 1989

[54] DISPOSABLE DIAPER HAVING SHIRRED EARS

[75] Inventors: Leigh E. Wood, Woodbury; Anthony J. Zoia, North Oaks, both of Minn.

[73] Assignee: Minnesota Mining and Manufacturing Company, St. Paul, Minn.

[21] Appl. No.: 290,846

[22] Filed: Dec. 29, 1988

Related U.S. Application Data

[63] Continuation of Ser. No. 219,803, Jul. 14, 1988, which is a continuation of Ser. No. 128,790, Dec. 4, 1987, abandoned.

[51] Int. Cl.$^4$ .............................................. A61F 13/16
[52] U.S. Cl. ................................... 604/389; 604/390; 428/230
[58] Field of Search ............... 604/389, 390, 385.1, 604/385.2, 366, 370; 428/230

[56] References Cited

U.S. PATENT DOCUMENTS

| | | | |
|---|---|---|---|
| 3,639,917 | 2/1972 | Althouse | 2/270 |
| 3,800,796 | 4/1974 | Jacob | 128/284 |
| 3,819,401 | 6/1974 | Massengale et al. | 156/85 |
| 3,860,003 | 1/1975 | Buell | 128/287 |
| 3,912,565 | 10/1975 | Koch et al. | 156/85 |
| 4,036,233 | 7/1977 | Kozak | 604/385.2 |
| 4,158,363 | 6/1979 | Schaar | 604/390 |
| 4,207,895 | 6/1980 | Schaar | 604/390 |
| 4,381,781 | 5/1983 | Sciaraffa et al. | 604/372 |
| 4,515,595 | 5/1985 | Kievit et al. | 604/385 A |
| 4,552,795 | 11/1985 | Hansen et al. | 428/110 |
| 4,563,185 | 1/1986 | Reiter | 604/385 A |
| 4,640,859 | 2/1987 | Hansen et al. | 428/105 |
| 4,652,487 | 3/1987 | Morman | 428/138 |
| 4,657,802 | 4/1987 | Morman | 428/152 |

FOREIGN PATENT DOCUMENTS

| | | |
|---|---|---|
| 2583620 | 6/1985 | France . |
| 2156656A | 10/1985 | United Kingdom . |
| 2108823A | 12/1985 | United Kingdom . |
| 2160473A | 12/1985 | United Kingdom . |

*Primary Examiner*—John D. Yasko
*Attorney, Agent, or Firm*—D. M. Sell; W. N. Kirn; C. Truesdale

[57] ABSTRACT

The back ears of a contoured disposable diaper are shirred to become stretchable and elastically retractable. Because of this, the diaper can be pulled snugly around the buttocks and the waist merely by applying ordinary fingertip pressure to the fastening tabs. The shirring can be provided by incorporating into the back ears of a flat diaper-forming blank a piece of heat-elasticizable material and then heating each diaper that is cut from the blank to shrink the piece. A preferred heat-elasticizable material comprises a substantially flat inelastic web to which is heat bonded a plurality of parallel elastomeric strands extended to at least about three times their relaxed length.

15 Claims, 3 Drawing Sheets

DISPOSABLE DIAPER HAVING SHIRRED EARS

This is a continuation of application Ser. No. 219,803 filed July 14, 1988, which is a continuation of application Ser. No. 128,790 filed Dec. 4, 1987, now abandoned.

BACKGROUND OF THE INVENTION

1 Field of the Invention

The invention concerns contoured disposable diapers, especially diapers having stretchable and elastically contractable leg cuffs and waist bands. The invention particularly involves the problem of attaining improved fit to the wearer at insignificantly increased cost of manufacture compared to diapers now on the market.

2. Description of the Related Art

Typically the body of a disposable diaper is substantially nonstretchable and has three major elements: a liquid permeable topsheet to be placed against the wearer's body, a liquid impermeable backsheet to form the face of the diaper, and an absorbent element interposed between the topsheet and backsheet. At the present time, those three elements are provided by three separate sheets, although it has been proposed to incorporate the absorbent and topsheet elements into a single sheet.

Most disposable diapers are contoured or formfitting and their leg cuffs and waistbands are elastically contractable as illustrated in U.S. Pat. No. 4,515,595 (Kievet et al.). Although the elastic waistbands of the Kievet et al. patent extend completely across both ends of the diaper, it is more common for the waist elastic to extend only part way across each end as in U.K. Pat. Application GB No. 2,156,656 (Pomplun et al.). In a contoured disposable diaper, the ends of the waist portions are flared out to form ears, and typically an adhesive-bearing fastening tab is attached to the back ears.

The fastening tabs of most contoured diapers are aligned with the substantially nonstretchable body of the diaper, as in the above-discussed patent and patent application. Forces applied by a user to pull the diaper snugly around the buttocks often result in tearing at the ears. In French Pat. Publication No. 2,583,620 (Courtray) which was laid open Dec. 25, 1986, the fastening tabs are aligned with an elastic waist band in order to make the diaper leakproof at the waist.

In the process of manufacturing disposable diapers, tension is typically maintained longitudinally, and elastic strips can be put into the leg cuffs in a stretched condition without difficulty, but the same is not true with waist strips which extend transversely where there is no tension. Accordingly, the waist of the diaper usually is made stretchable and elastically contractable by adhering to the backsheet a flat strip of heat-elasticizable material, i.e., a material which is heat-shrinkable and then can be stretched elastically to its original unshrunk dimensions. Then, after cutting out the diaper, the diaper is heated to shrink the heat-elasticizable material, thus shirring the waist band. When the heat-elasticizable material is a plastic film which also is heat-sealable, it can be adhered to the backsheet either adhesively or by being heat-sealed to the backsheet.

A preferred heat-elasticizable material for shirring the waist is disclosed in U.S. Pat. No. 4,552,795 (Hansen et al.). Before being shirred, it comprises a substantially flat inelastic web to which has been heat-bonded a plurality of parallel elastomeric strands that have been extended to at least about three times their relaxed length. The strand-bearing web can be coated with a layer of pressure-sensitive adhesive to adhere it to the backsheet.

Instead of the waist band being stretchable and elastically contractable, some disposable diapers employ stretchable fastening tapes as in U.S. Pat. No. 3,800,796 (Jacob). Although the diaper of the Jacob patent is not contoured, stretchable fastening tapes have been used on disposable diapers which are contoured.

U.S. Pat. No. 4,381,781 (Sciaraffa et al.) says that when there is an elastic waist strip, "the folding of the diaper waist end, which must take place after the continuous web is cut into individual diapers, is extremely difficult to accomplish. This is because the leg elastic will retract the individual diaper lengthwise if it is not held entirely flat while moving rapidly along the production line until packaging and the folding operation while simultaneously holding the diaper flat cannot be done readily" (col. 1, lines 35-47). The Sciaraffa et al. patent avoids an elastic waist strip, by cutting, as shown in FIG. 1, "openings 70 and 72 through the joined topsheet 2 and backsheet 4. The openings 70 and 72 intersect the waist edge 18 such that there is no diaper material between each of the openings 70 and 72 and the waist edge 18 . . . Elastic layer material such as layers 78 and 80 is respectively disposed in the openings 70 and 72 and affixed to either the topsheet 2 or backsheet 4, or both, so that the layers 78 and 80 become an integral part of the diaper as shown in FIG. 7" (col. 4. lines 7-19). The "elastic layers 78 and 80 may respectively be located entirely or partially within the ears 42 and 44 or entirely laterally inward of the ears 42 and 44" (col. 4, lines 41-44). "Due to the inelasticity of the topsheet 2 and backsheet 4, or both, most of the transverse tensile stress is applied to the elastic layer 80 causing it to stretch and provide a snug fit between the skin of the wearer and the waist areas 8 and 10" (col. 5. lines 5-10).

The Sciaraffa et al. patent says: "The attaching of the elastic material to the back sheet and/or top sheet of the diaper requires only cutting the sheets as they move in web form, cutting the elastic material, and pressing the elastic material against one of the sheets. These manufacturing steps are all readily accomplished in conjunction with the usual high speed diaper production lines" (col. 2, lines 32-38). No mention is made of the need to maintain good registration and probable difficulties in attempting to do so. It is believed that the diaper of the Sciaraffa et al. patent has not appeared on the market.

SUMMARY OF THE INVENTION

The invention provides a contoured disposable diaper which can be pulled snugly around the buttocks and the waist merely by applying ordinary fingertip force to the fastening tabs. The resulting improved fit is achieved while minimizing the problem of accidental tearing and is accompanied by both better appearance and enhanced performance. The novel diaper is believed to be the first disposable diaper which provides those advantages and yet can be manufactured at substantially the same cost as disposable diapers now on the market. Like those now on the market, the body of the diaper of the invention is generally substantially nonstretchable and has a liquid permeable topsheet, a liquid impermeable backsheet, and an absorbent element interposed between the topsheet and backsheet. As noted above, the absorbent and topsheet elements might be incorporated into a single sheet. At least one of the topsheet and backsheet is flared to form a pair of back ears. A fastening tab, which preferably is substantially nonstretchable, is attached to each of the back ears.

The diaper of the invention differs from prior contoured disposable diapers in that at least one of its back ears is elastically shirred in an area aligned with its fastening tab to permit it to be stretched elastically at least one cm under ordinary fingertip force applied to the fastening tab. The shirred area, in an infant diaper of average size, should extend over a height of at least 3 cm (preferably from 4 to 8 cm). For the smallest infant diapers, the shirring height should be at least 2 cm, and for an adult diaper of average size, the shirring height should be at least 6 cm. By "height" is meant the direction between the waist and the crotch of the diaper. "Ordinary fingertip force" may range from about 200 to 2000 grams of force.

The elastic shirring preferably is provided by adhering to the backsheet or topsheet, or both, a heat-elasticizable material, preferably including a plurality of parallel elastomeric strands as in the above-cited Hansen et al. patent. The force necessary to stretch the elastically shirred ear at least one cm can be controlled by the modulus of the heat-elasticizable material in its heat-elasticized state, its width, its thickness, or combinations thereof. Upon stretching an elastically shirred ear close to its elastic limit, the user feels an abrupt increase in force necessary to continue to elongate the ear. The diaper should be designed so that when this abrupt increase is felt, sufficient tension has been applied to realize a snug fit around the wearer's buttocks and waist, and the user should realize that additional force is unnecessary. This should greatly reduce the hazard of tearing of the ears as compared to disposable diapers now on the market. Preferably, this abrupt increase in tension is felt at from 500 to 1500 grams of force for an infant diaper of average size.

Because the novel diaper can be easily pulled snugly around the buttocks and waist, there should be no need for an elastically contractable waist band, thus saving the cost of elasticizing the waist.

The diaper of the invention can be manufactured with equipment now in widespread use, e.g., as shown and described in U.S. Pat. No. 4,563,185 (Reiter). This can be accomplished merely by adding to the line one station at which small pieces of heat-elasticizable material are adhered to the backsheet adjacent at least one of its edges. When using equipment including a station at which a strip of heat-elasticizable material is applied at the waist, that station can be modified so that instead of applying material at the waist, a small piece of heat-elasticizable material is applied at each back ear. Alternatively, that station can be modified to apply a U-shaped strip across the waist, with the ends of the U providing the elastic shirring across the ears. Because the cutting of U-shaped strips might involve greater waste of raw material than the application of three separate pieces, it may be more economical to modify the station to apply three pieces simultaneously. The back ears become elastically shirred at the end of the assembly portion of the diaper line where the diapers are exposed to heat, there used to shirr the waist band as described in the above-cited Reiter patent.

DETAILED DESCRIPTION

Preferably the shirr across each back ear is at least 4 cm in height in order to spread the tension applied to the fastening tabs across a large area at each side of the rear of the diaper. This ensures a snug fit around the buttocks and waist merely by applying ordinary fingertip pressure to the fastening tabs. Before being heated, the heat-elasticizable material should be at least 2 cm, preferably at least 3 cm, in width in the circumferential direction of the diaper in order to permit the ear to be stretched at least one cm under ordinary fingertip force. It may be economically wasteful in infant diapers for the heat-elasticizable material to be more than 6 cm in width before the shirring.

As compared to the need to maintain good registration in making the diaper of the above-discussed Sciaraffa et al. patent, the pieces of heat-elasticizable material applied to the back ears of the novel diaper need not be applied with precision, just as precision is unnecessary in applying heat-elasticizable waist strips in current diaper manufacture. In order to allow substantial errors in applying pieces of the heat-elasticizable material to the ears, their application preferably is programmed to leave a space of at least 0.5 cm between the piece and the edge of the waist, thus ensuring that no piece will extend into the front waist region of the adjacent diaper. Except for economy, it is unnecessary to leave a space between the heat-elasticizable material and the leg openings if the heat-elasticizable material is applied before the leg openings are cut out.

In order to keep costs to a minimum by conserving material, the heat-elasticizable material preferably extends only about half the height of each back ear, e.g., from 4 to 8 cm, as compared to the height of the ears of an infant diaper of average size being about 10–15 cm. Preferably the heat-elasticizable material is at the center of the height of the ear, and the fastening tab is aligned with the piece of heat-elasticizable material. When the ear is elastically shirred by exposing the heat-elasticizable material to heat, the ear becomes inelastically shirred across the rest of its height.

THE DRAWING

The invention may be more understandable by reference to the drawing, all figures of which are schematic, wherein.

Figure 1:
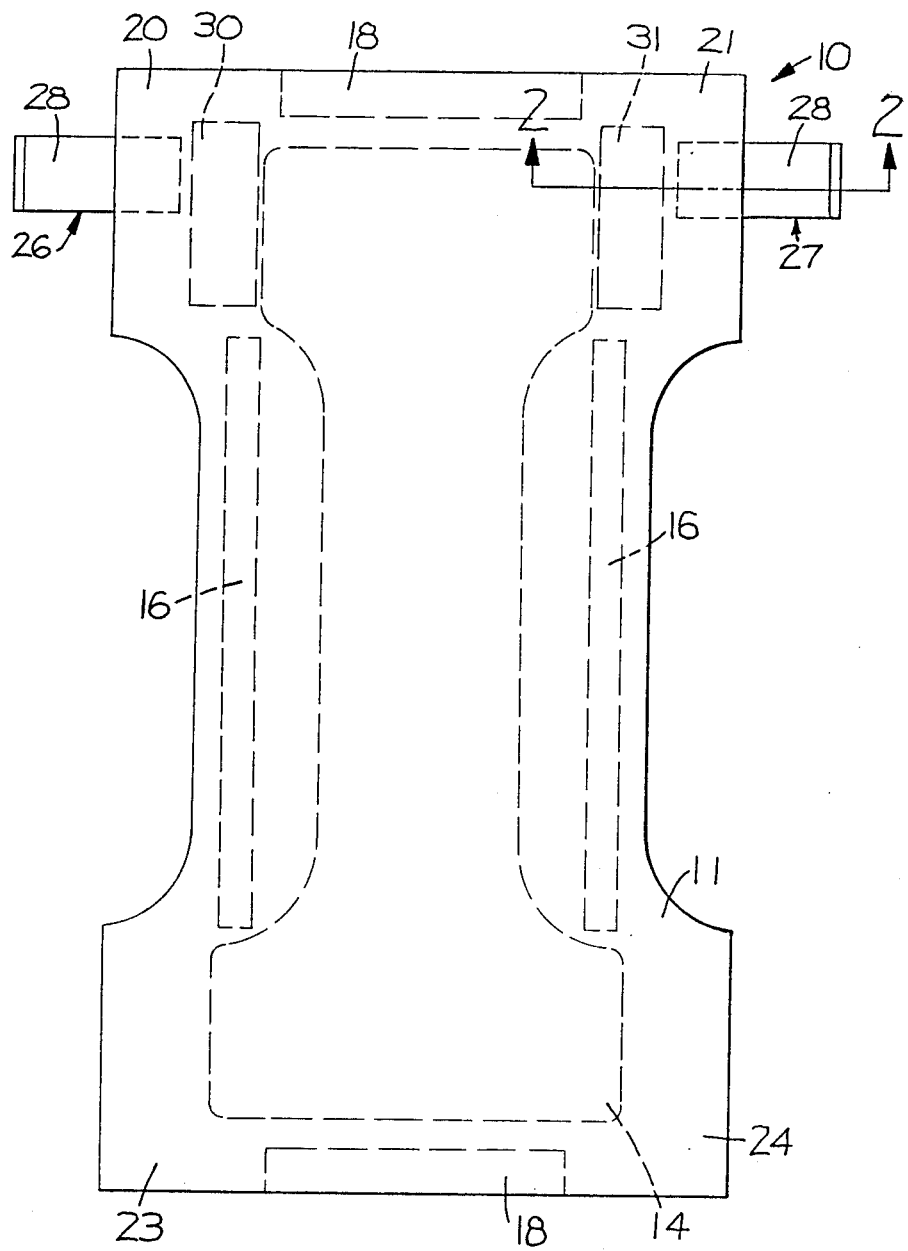
FIG. 1 is a plan view of a first contoured disposable diaper of the invention in a flat condition, partly broken away.

The body of the diaper 10 shown in FIGS. 1–3 and 5 is made up of a liquid permeable topsheet 11 to be placed against the wearer's body, a liquid impermeable backsheet 12 to form the face of the diaper, and an absorbent element 14 interposed between the topsheet and backsheet. Also interposed between the topsheet and backsheet are elastically contractable strips 16 and 18 at the leg cuffs and waist bands, respectively. As in most contoured disposable diapers now on the market, the elastically contractable strips 16 at the leg cuffs are applied in a stretched condition while those 18 at the waist bands are heat-elasticizable material that does not become elastically contractable until it has been heat-shrunk. The ends of the waist portions of the diaper 10 are flared out to form back ears 20 and 21 and front ears 23 and 24. Attached to the back ears 20 and 21 are fastening tabs 26 and 27, respectively. Each fastening tab bears a layer of pressure-sensitive adhesive 28 by which it can be secured to the front of the diaper. Pieces 30 and 31 of heat-elasticizable material are adhered to the backsheet 12 at each of the back ears 20 and 21, respectively, by a layer of pressure-sensitive adhesive 32.

Figure 2:
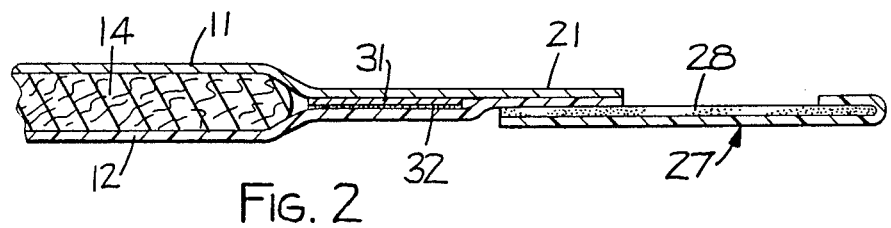
FIG. 2 is a cross section along line 2—2 of FIG. 1.
Figure 3:
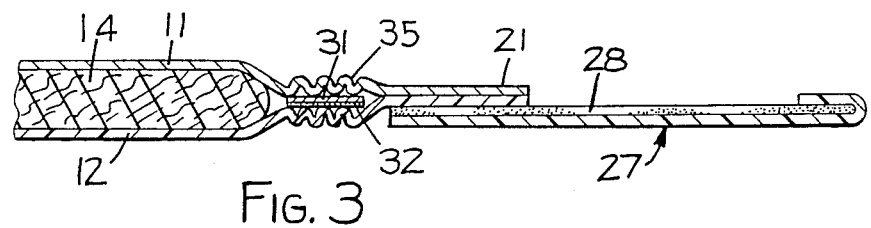
FIG. 3 is a cross section similar to that of FIG. 2 except after shirring.
Figure 5:
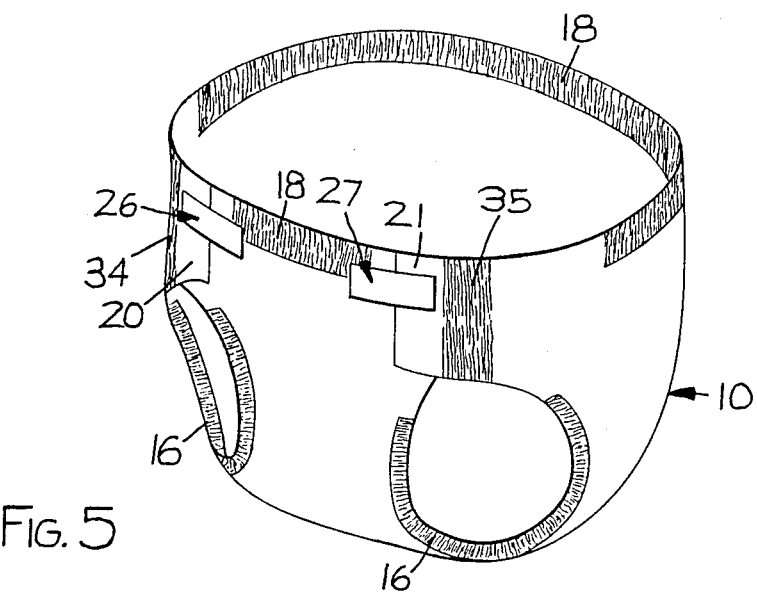
FIG. 5 is a perspective view of the diaper of FIGS. 1–3 in the configuration it would assume when being worn by a person.

After the diaper 10 has been formed flat as shown in FIGS. 1 and 2, it is heated to heat-shrink the waist strips 18 and the pieces 30 and 31 of heat-elasticizable material. Shrinkage of the latter causes elastic shirring 34 and 35 of the ears 20 and 21, respectively, as best seen in FIGS. 3 and 5.

Figure 4:
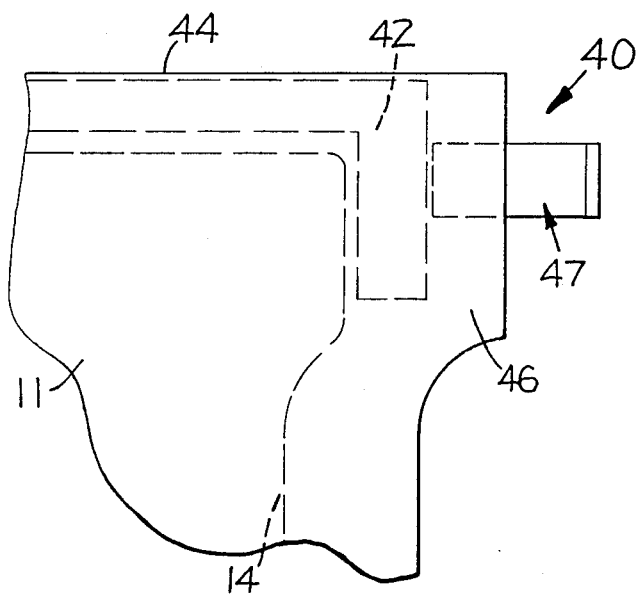
FIG. 4 is a plan view of the ear and waist portions of a second contoured disposable diaper of the invention in a flat condition, partly broken away.

The diaper 40 shown fragmentally in FIG. 4 is identical to that of FIGS. 1–3 and 5 except that it employs a single U-shaped piece 42 of heat-elasticizable material instead of two separate pieces. When the diaper 40 is heated, shrinkage of the U-shaped piece 42 will shirr both the waist band 44 and the back ear 46. The diaper 40 has fastening tabs 47 similar to those of the diaper 10.

Suitable heat-elasticizable materials for use in providing the heat-activated elastic shirring of the back ears 20 and 21 includes elastic films such as flexible polyurethanes as described in U.S. Pat. No. 3,912,565 (Koch et al.), plasticized vinyl chloride polymers as described in U.S. Pat. No. 3,819,401 (Massengale et al.), copolymers of alternating polyamide and polyether blocks as described in U.K. Pat. Appl. No. 2,160,473A (Matray et al.), and other block copolymers as described in U.S. Pat. No. 3,639,917 (Althouse). Also suitable are the elastic composite films of U.S. Pat. No. 4,652,487 (Mormon), U.S. Pat. No. 4,657,802 (Mormon), and U.S. Pat. No. 4,640,859 (Hansen et al.).

The piece of heat-elasticizable material should shrink at least 30% when heated, thus permitting the back ear to be stretched elastically at least 30% the width of the piece of heat-elasticized material. Preferably the heat-elasticized material shrinks about 50%.

EXAMPLE

The heat-elasticizable material used in this Example is a flat inelastic web to which had been heat-bonded a plurality of parallel elastomeric strands extended to at least about three times their relaxed length as disclosed in the above-cited Hansen et al. patent. This material was cut to pieces having a length of 2 inches (5 cm) and a width of 2 inches (5 cm). To each piece was laminated a layer of pressure-sensitive adhesive.

The topsheet of a commercially available diaper ("Luvs" brand disposable diaper from Proctor and Gamble Co.) was mechanically separated from the backsheet in a rear end region. The adhesive side of a piece of heat-elasticizable material was then adhered to the inside face of the backsheet of the diaper, after which the rear end was reassembled, reattaching the topsheet to the backsheet by using a thin strip of pressure-sensitive adhesive. The width and the strands of the piece of heat-elasticizable material were oriented in the circumferential direction of the diaper (transverse to the height of the ear). The diaper was then placed in a current of circulatory hot air (200° F., 93° C.) for 40 seconds. The ear portion of the diaper shirred, and the width of the piece of heat-elasticizable material was reduced to 1.06 inches (2.7 cm), a shrinkage of 47%.

Figure 6:
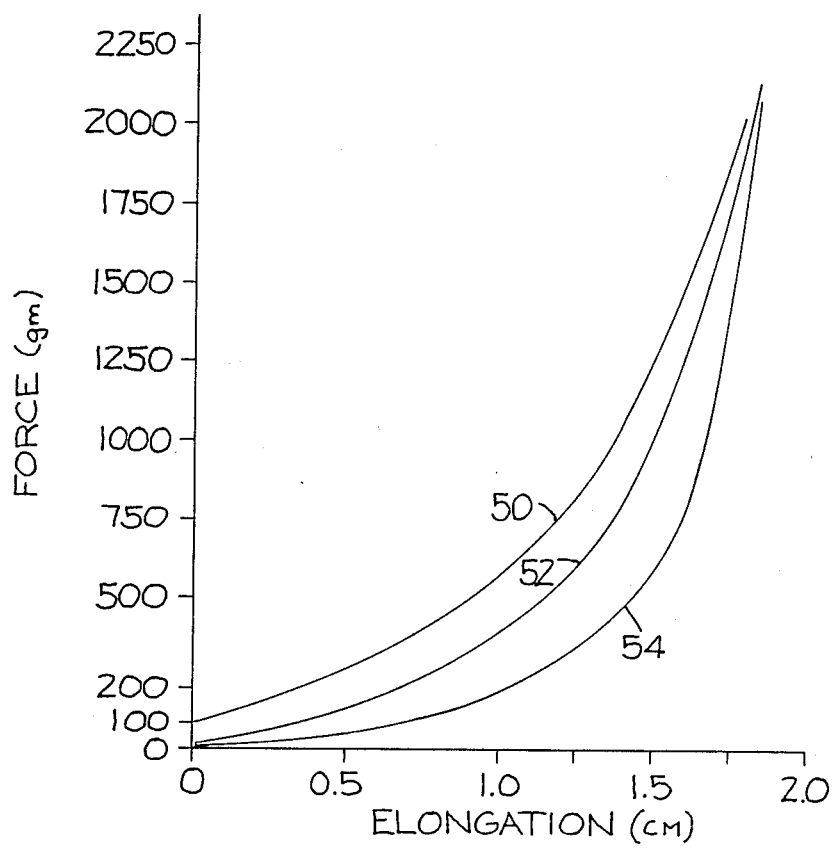
FIG. 6 shows a cycled stress-strain curve for the shirred ear of a preferred diaper of the invention.

A cycled stress-strain curve for the shirred ear of the diaper of this Example is shown in FIG. 6. This curve was made in an Instron tensile tester, the lower jaw of which extended across the full width of the fastening tape while the upper jaw (7.5 cm in width) clamped the center of the diaper from the top toward the crotch. In doing so, the shirred ear was slightly stretched to ensure against any slack. The upper jaw was moved away from the lower jaw at a speed of 10 inches (25 cm) per minute. In FIG. 6, line 50 shows the first pull, line 52 shows the second and subsequent pulls, and line 54 shows the relaxation curve. Lines 50 and 52 indicate that when stretching of the shirred ear approaches its elastic limit, a user of the diaper would be warned that substantially increased force might accidentally tear the ear.

While the diaper shown in the drawing employs pressure-sensitive adhesive fastening tabs, other fastening means such as snaps or hook-and-loop fasteners are also useful in diapers of the invention.

Although the Example and the drawings illustrate the use of adhesive to affix heat-elasticizable material to either the topsheet or backsheet of the diaper of the present invention, alternate methods such as heat bonding and sonic welding can also be employed.

We claim:

1. A contoured diaper, which comprises a liquid permeable topsheet, a liquid impermeable backsheet, and an absorbent element interposed between the topsheet and backsheet, at least one of the topsheet and backsheet being flared to form a pair of back ears, each back ear having a fastening tab, at least one of the back ears being elastically shirred in an area aligned with its fastening tab, which shirring extends over a height of at least 3 cm and permits the back ear to be stretched elastically at least one cm under ordinary fingertip force applied to the fastening tab.

2. Diaper as defined in claim 1 wherein both back ears are shirred.

3. Diaper as defined in claim 2 wherein the shirr across each back ear is at least 4 cm in height.

4. Diaper as defined in claim 3 wherein the shirr is provided by a piece of heat-elasticizable material adhered to at least one of the topsheet and backsheet.

5. Diaper as defined in claim 4 wherein said back ear can be stretched elastically at least 30% of the width of the piece of heat-elasticizable material.

6. Diaper as defined in claim 4 wherein the heat-elasticizable material at each ear is contiguous with a strip of the heat-elasticizable material extending across the waistband.

7. Diaper as defined in claim 4 wherein the heat-elasticizable material at each ear is a separate piece.

8. Diaper as defined in claim 4 wherein the heat-elasticizable material bears a layer of pressure-sensitive adhesive by which it is adhered to the backsheet.

9. Diaper as defined in claim 8 wherein the heat-elasticizable material before being shirred comprises a substantially flat inelastic web to which is heat-bonded a plurality of parallel elastomeric strands extended to at least three times their relaxed length.

10. Method of making contoured disposable diapers comprising three major elements: a liquid permeable topsheet, a liquid impermeable backsheet, and an absorbent element interposed between the topsheet and backsheet, in which method great lengths of said elements are moved in the direction of their lengths, said method comprising the steps of:

(1) adhering to at least one of said topsheet and backsheet, adjacent at least one of its edges, spaced-apart flat pieces of heat-elasticizable material, (2) continuously bonding said elements together into a coherent body, (3) cutting out individual diapers from said body to form a back ear at each adhered piece of heat-elasticizable material, and (4) heating the diapers to shrink said pieces of heat-elasticizable material and thus elastically shirr the body of each diaper at a back ear.

11. Method as defined in claim 10, in step (1) of which pieces of heat-elasticizable material are adhered in pairs adjacent opposite edges of said topsheet and backsheet.

12. Method as defined in claim 10, in step (1) of which each piece of heat-elasticizable material is U-shaped and is adhered with the ends of each U adjacent opposite edges of said backsheet.

13. Method as defined in claim 10 wherein the heat-elasticizable material shrinks at least 30% in step (4).

14. Method as defined in claim 10 wherein said flat pieces of heat-elasticizable material comprise a substantially flat inelastic web to which is heat bonded a plurality of parallel elastomeric strands extended to at least about three times their relaxed length.

15. Method as defined in claim 10 wherein said flat pieces of heat-elasticizable material bear a layer of pressure-sensitive adhesive by which it is adhered to at least one of said topsheet and backsheet.

* * * * *